Nov. 25, 1975
C. F. ZAIGER
CHERRY TREE
Filed Jan. 9, 1975
Plant Pat. 3,810
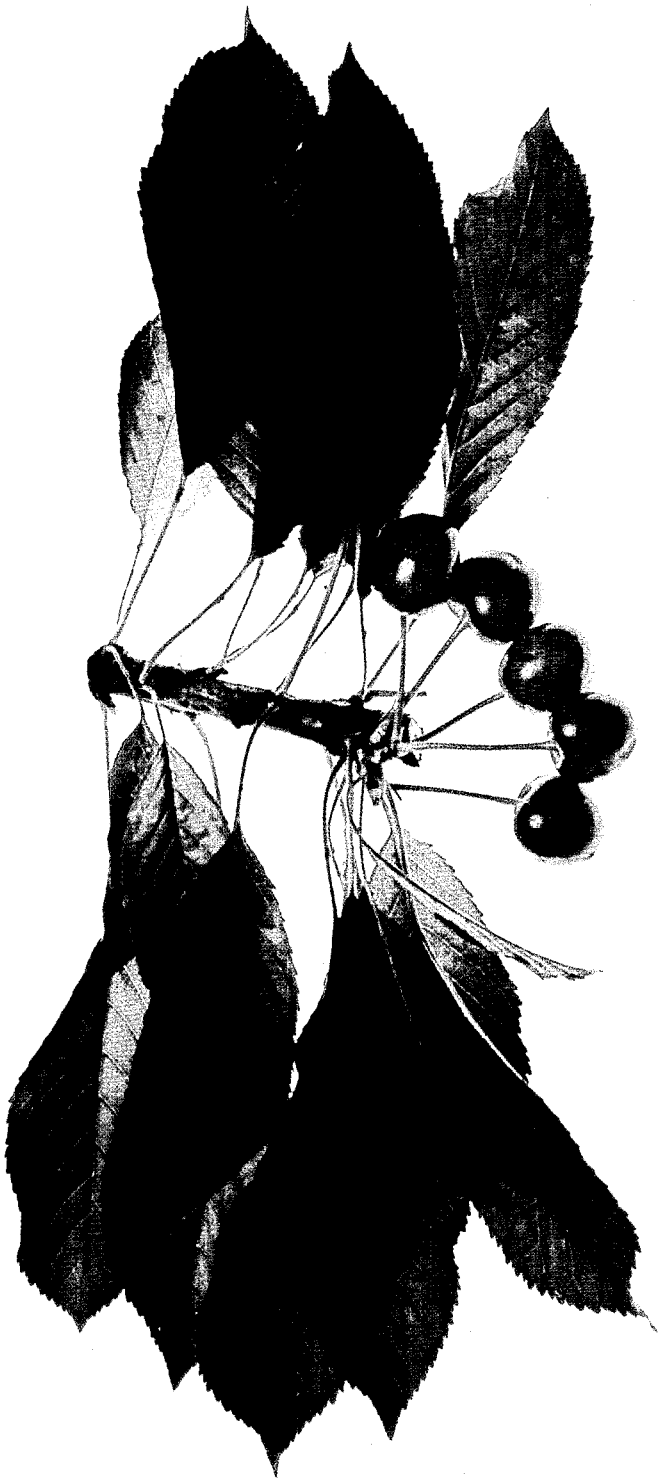

United States Patent

Plant Pat. 3,810
Patented Nov. 25, 1975

3,810
CHERRY TREE

Chris Floyd Zaiger, 537 Rosemore Ave.,
Modesto, Calif. 95351

Filed Jan. 9, 1975, Ser. No. 539,769
Int. Cl. A01h *5/03*
U.S. Cl. Plt.—37 1 Claim

ABSTRACT OF THE DISCLOSURE

A variety of cherry tree which has dwarf characteristics, close leaf nodes, short heavy branches, stocky trunk, and bears large red fruit of good eating quality.

ORIGIN OF VARIETY

The present variety of cherry tree is a bud sport from a seedling cherry tree grown by me in my experimental orchard located in Modesto, Stanislaus County, Calif. Subsequent to recognition by me of the novel characteristics—which will hereinafter appear—of said bud sport, I propagated the variety in anticipation of ultimate introduction to the home garden trade and to meet the existing demand for a dwarf cherry tree with large red fruit of good eating quality.

ASEXUAL REPRODUCTION OF THE VARIETY

The present variety of cherry tree was asexually reproduced by me—in my said experimental orchard—by budding, and such reproductions ran true to the original bud sport.

SUMMARY OF THE VARIETY

The present variety of cherry tree bears large red fruit of good eating quality. The tree is of dwarf characteristics, close leaf nodes, short heavy branches, stocky trunk. The variety of tree has the dwarf characteristics of an attractive ornamental and produces desirable large, firm, red fruit.

BRIEF DESCRIPTION OF THE DRAWING

The drawing is an illustration, by photographic reproduction in color, showing a portion of branch with leaves and fruit. The leaves showing their upper and lower surfaces, the petiole and glands. The cluster of the fruit showing the shape, surface color, and stem.

DESCRIPTION OF THE VARIETY

The botanical details of this new and distinct variety of cherry tree—with color definitions (except those of common color terms) referenced to Reinhold Color Atlas by A. Korneruf and J. H. Wanscher—are as follows:

Tree:
- *Size.*—Dwarf—approximately ⅓ of normal size.
- *Vigor.*—Non-vigorous.
- *Growth.*—Upright.
- *Density.*—Heavily dense.
- *Production.*—Productive.

Trunk:
- *Size.*—Stocky.
- *Texture.*—Medium.

Branches:
- *Size.*—Stocky, upright.
- *Lenticels.*—Number: Few, medium size.

Leaves:
- *Size.* — Medium. Average length — 4¾" to 5¾". Average width—2" to 2¾".
- *Form.*—Ovate. Acutely pointed.
- *Thickness.*—Thick.
- *Margin.*—Coarsely serrate.
- *Petiole.*—Long. Thick.
- *Glands.*—Average number—2. Primarily on petiole. Reniform.
- *Color.* — Top side — Grayish green to dark green (28E6 to 29F6). Under side—Grayish green to dull green (28D5 to 29E5).

Flower buds:
- *Size.*—Large.
- *Length.*—Medium.
- *Form.*—Plump.

Flowers:
- *Blooming period.*—Date of first bloom; Mar. 22, 1974. Date of full bloom: Mar. 26, 1974.
- *Color.*—White.

Fruit:
- *Maturity when described.*—Eating ripe, June 20.
- *Size.* — Uniform. Large. Average diameter axially 1 3/16". Average transversely in suture plane 1 5/16".
- *Form.*—Uniform. Globose to slightly oblate. Substantially no doubles.
- *Suture.*—*Shallow.*
- *Ventral surface.*—Rounded slightly.
- *Cavity.*—Wide. Flaring.
- *Base.*—Rounded.
- *Apex.*—Slightly depressed.

Skin:
- *Thickness.*—Medium.
- *Texture.*—Tough to medium.
- *Down.*—Wanting.
- *Color.*—Claret 11D8.

Flesh:
- *Texture.*—Firm. Crisp. Meaty.
- *Ripens.*—Even.
- *Flavor.*—Subacid.
- *Eating quality.*—Good.
- *Color.*—Geranium Red 11B7.

Stone:
- *Type.*—Semi-free.
- *Size.*—Average length—7/16". Average breadth—⅜". Average thickness—¼".
- *Form.*—Oblong.
- *Tendency to split.*—None.

Use: Market. Local. Dessert.
Keeping quality: Very Good.

The tree and its fruit herein described may vary in slight detail due to climatic and soil conditions under which this variety may be grown; the present description being of the variety as grown at Modesto, Stanislaus County, Calif.

I claim:

1. A new and distinct variety of cherry tree, as illustrated and described, bearing large, red, firm fruit of good eating quality; by a tree with dwarf characteristics of close leaf nodes, short heavy branches, and a stocky trunk.

No references cited.

ROBERT E. BAGWILL, Primary Examiner